US006153639A

United States Patent [19]
Sternberg et al.

[11] Patent Number: 6,153,639
[45] Date of Patent: *Nov. 28, 2000

[54] ETHYLENE GLYCOL ESTERS AS PHOTOACTIVE AGENTS

[75] Inventors: Ethan Sternberg; David Dolphin; Julia G. Levy; Anna M. Richter, all of Vancouver; David W. C. Hunt, White Rock; Ashok Jain, Vancouver; Elizabeth M. Waterfield, Vancouver; Ronald E. Boch, Vancouver, all of Canada

[73] Assignees: QLT PhotoTherapeutics Inc.; The University of British Columbia, both of Canada

[*] Notice: This patent is subject to a terminal disclaimer.

[21] Appl. No.: 09/313,106

[22] Filed: May 17, 1999

Related U.S. Application Data

[63] Continuation of application No. 09/088,524, Jun. 1, 1998, Pat. No. 5,929,105, which is a continuation-in-part of application No. 08/852,494, May 7, 1997, abandoned.

[51] Int. Cl.⁷ .................................................. A61K 31/40

[52] U.S. Cl. .......................... 514/410; 514/412; 514/414; 514/415; 514/419; 514/422; 608/88; 608/89; 608/94; 608/95

[58] Field of Search ................................. 514/410, 412, 514/414, 415, 419, 422; 604/88, 89, 94, 95

[56] References Cited

U.S. PATENT DOCUMENTS

| | | | |
|---|---|---|---|
| 4,883,790 | 11/1989 | Levy et al. | 540/145 |
| 4,920,143 | 4/1990 | Levy et al. | 514/410 |
| 5,095,030 | 3/1992 | Levy et al. | 514/410 |
| 5,171,749 | 12/1992 | Levy et al. | 514/410 |
| 5,283,255 | 2/1994 | Levy et al. | 514/410 |
| 5,399,583 | 3/1995 | Levy et al. | 514/410 |
| 5,498,710 | 3/1996 | Pandey et al. | 540/145 |

FOREIGN PATENT DOCUMENTS

| 352 076 | 1/1990 | European Pat. Off. |
|---|---|---|
| 9015 059 | 12/1990 | WIPO . |

OTHER PUBLICATIONS

Mosmann, T. et al., *J. Immunol. Meth.* (1983) 65:55–63.

*Primary Examiner*—Frederick Krass
*Attorney, Agent, or Firm*—Morrison & Foerster

[57] ABSTRACT

New compounds useful in photodynamic therapy are of the formula

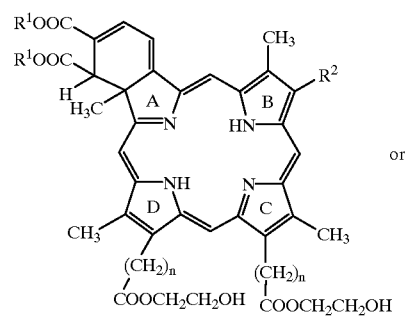

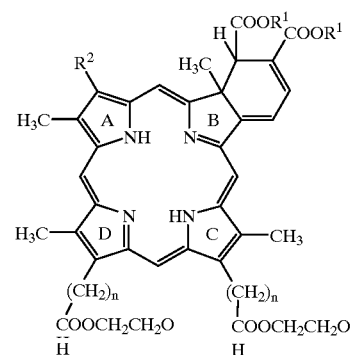

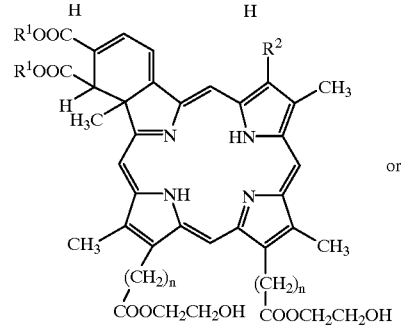

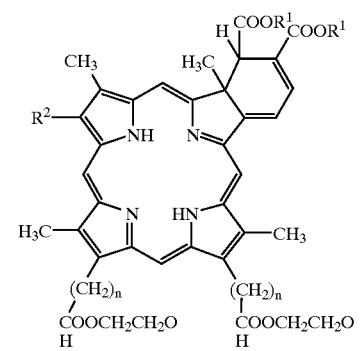

and their 1,4-diene isomers
and the metallated and/or labeled and/or conjugated forms thereof
wherein each $R^1$ is independently alkyl (1–6C);
each n is independently an integer of 0–6; and
$R^2$ is vinyl or a derivative form thereof.

24 Claims, 16 Drawing Sheets

ETHYLENE GLYCOL ESTERS AS PHOTOACTIVE AGENTS

This application is a continuation of U.S. Ser. No. 09/088,524, filed Jun. 1, 1998 and now U.S. Pat. No. 5,929,105, which is a continuation-in-part of U.S. Ser. No. 08/852,494, filed May 7, 1997 and now abandoned, the contents of both applications being incorporated by reference herein.

TECHNICAL FIELD

The invention relates to compounds useful in photodynamic therapy (PDT) and related applications. In particular, it concerns ethylene glycol esters of monohydrobenzoporphyrins.

BACKGROUND ART

Photodynamic therapy (PDT) generally involves the administration of compounds that are capable of absorbing light, typically in the visible range, but also in the near ultraviolet, followed by irradiation of locations in the subject for which a toxic or inhibitory effect is desired. PDT was initially developed using hematoporphyrin and related compounds in the treatment of tumors, as it appeared that these compounds would "home" to locations containing rapidly dividing cells. The tumor could then be irradiated with light absorbed by the hematoporphyrin and destruction of the surrounding tissue resulted. PDT has since been shown to be useful for treatment of atherosclerotic plaques, restenosis, infections in the blood stream, rheumatoid arthritis, psoriasis and in the treatment of ocular conditions not necessarily limited to tumors.

U.S. Pat. No. 5,171,749 and patents issuing on related applications, U.S. Pat. Nos. 5,283,255; 5,399,583; 4,883,790; 4,920,143; and 5,095,030; all of which are incorporated herein by reference, describe and claim a class of photoactive compounds useful in PDT designated the monohydrobenzoporphyrins, or "BPDs." This class is obtained by Diels-Alder reaction of a mono- or disubstituted alkyne with protoporphyrin-IX and the resultant compounds can further be isomerized, reduced, and/or derivatized to obtain a large class of BPDs. As disclosed in these patents, a particularly useful subclass of this group results from hydrolysis or partial hydrolysis of the ester groups of the 2-carboxyethyl side-chains on rings C and D. Esterification as protection of these groups during the Diels-Alder reaction results in initial products which contain 2-carbalkoxyethyl groups. It was found that facile hydrolysis of these esters could readily be conducted, leaving any carbalkoxy groups associated with the Diels-Alder product obtained from a dicarbalkoxyalkyne virtually completely unhydrolyzed. This resulted in four species of compounds, BPD-MA, BPD-MB, BPD-DA and BPD-DB as depicted in FIG. 1; this figure taken from U.S. Pat. No. 10 5,171,749. In this depiction, $R^1$ and $R^2$ are carbalkoxy groups, typically carbomethoxy or carboethoxy, and R is alkyl (1–6C).

BPD-MA was found to have particularly useful properties for PDT and is currently in clinical development. However, there remains a need for additional specific forms of photoactive agents which expand the repertoire of photoactive compounds for the variety of indications to which PDT is applied, as noted above. The present invention provides compounds in which rings C and D contain ethylene glycol esters of the carboxyalkyl substituents. These compounds have pharmacokinetic properties which are advantageous in certain instances where PDT is employed.

DISCLOSURE OF THE INVENTION

The compounds of the invention are useful new additions to the repertoire of compounds that find application in photodynamic therapy and related methodologies that employ photoactive compounds. The presence of ethylene glycol esters in these molecules provides them with characteristics that permit expansion of the scope of conditions under which such photoactive compounds are employed and fine tuning of the treatment.

Thus, in one aspect, the invention is directed to compounds of the formula

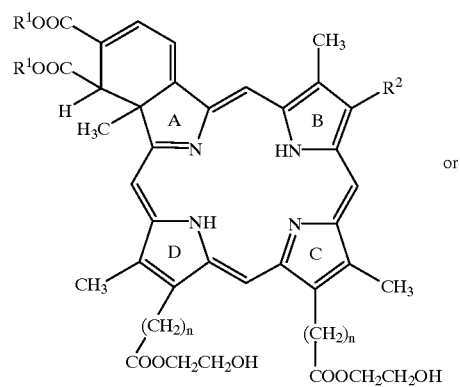

or

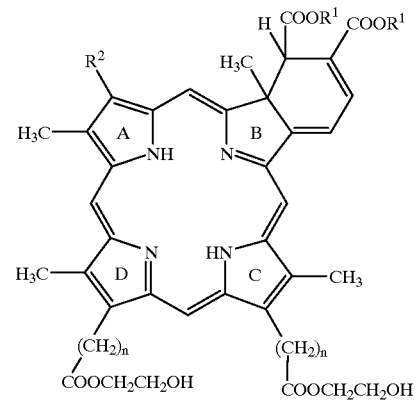

and the metallated and/or labeled and or conjugated forms thereof
wherein $R^1$ is alkyl (1–6C), preferably methyl, n is an integer of 0–6, preferably 2, and $R^2$ is vinyl or a derivative thereof, preferably vinyl.

The invention also is directed to compounds of the formula

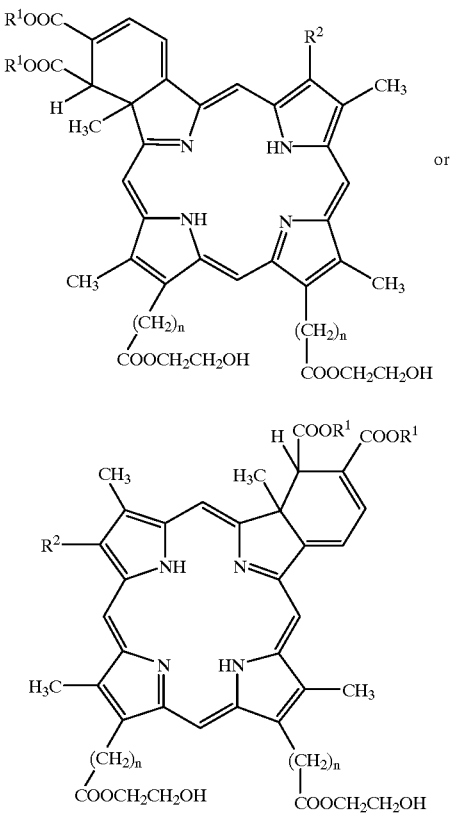

and the metallated and/or labeled and or conjugated forms thereof wherein $R^1$, n, and $R^2$ are defined as described above. These analogs are derived from protoporphyrin III and protoporphyrin XIII respectively, in a manner similar to that in which the compounds of formulas 1 and 2 are derived from protoporphyrin IX. The invention also includes isomers of the various forms of formulas 1–4 which result from the unrearranged Diels-Alder condensation products (i.e., the 1,4-diene) as described in U.S. Pat. No. 4,883,790, incorporated herein by reference. These structures are also set forth in FIG. 14.

In other aspects, the invention related to methods of diagnosis and treatment using the compounds of formula 1, 2, 3 or 4 or their 1.4-diene isomers, as shown in FIG. 14, or mixtures thereof.

MODES OF CARRYING OUT THE INVENTION

Figure 1:
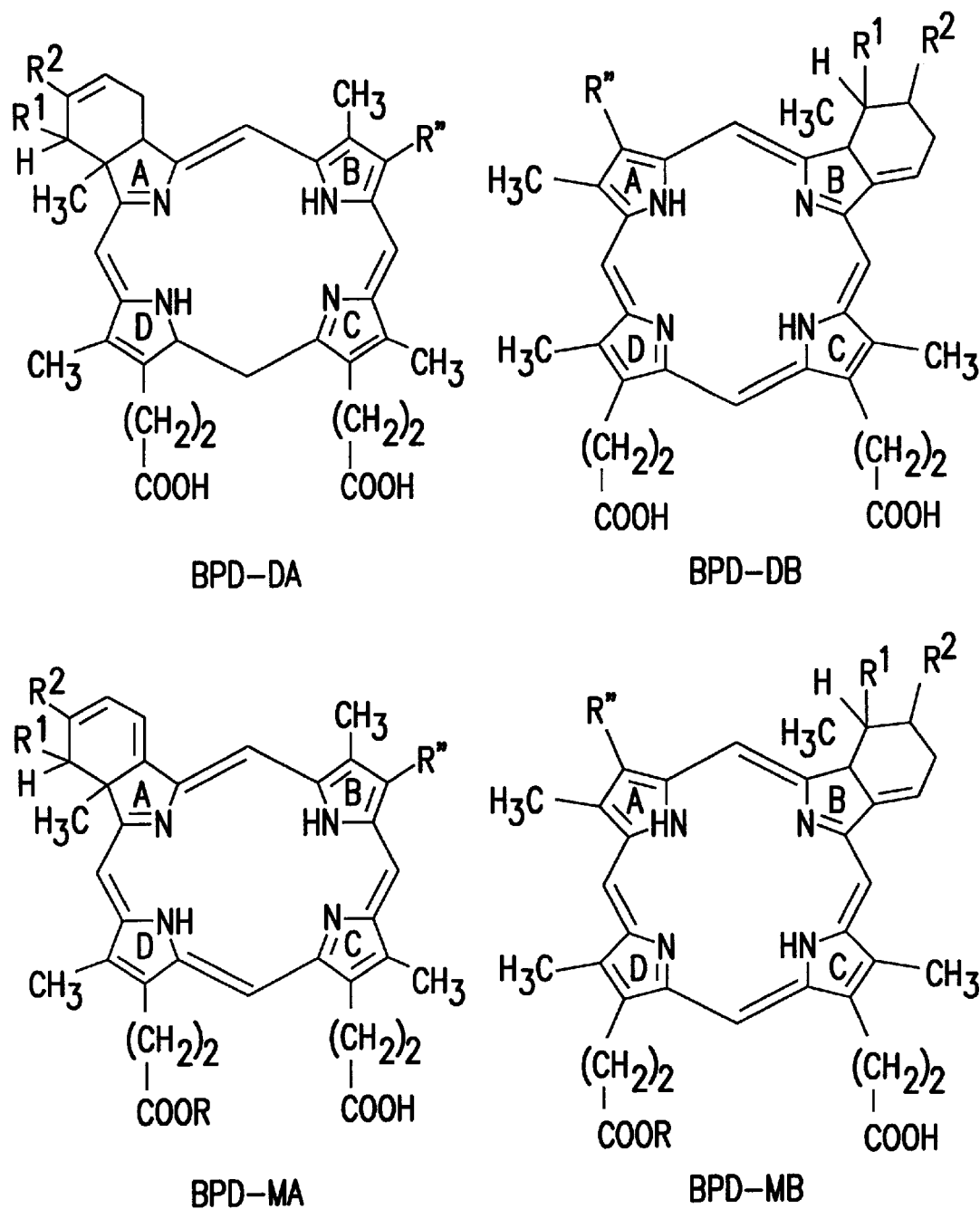
FIG. 1 shows the compounds of the prior art, BPD-MA, BPD-MB, BPD-DA and BPD-DB.

The compounds of the invention are related to those disclosed in the BPD patents cited above, but differ in that they contain esters of ethylene glycol in the substituents on rings C and D. These compounds can be prepared by simple hydrolysis of the carbalkoxyalkyl or carbalkoxyl substituents and reesterification of the resulting carboxyl groups in the C and D rings of the benzoporphyrins, or can be obtained directly by transesterification.

It will be noted that compounds 1 and 2 and their 1,4-diene isomers are individual species of the genus, described in the above-referenced U.S. patents, obtained through-a process which comprises a Diels-Alder reaction with protoporphyrin IX. Compounds 3 and 4 and their 1,4-diene isomers are prepared in a completely analogous manner but using protoporphyrin III or protoporphyrin XIII as substrates for the Diels-Alder reaction. Since protoporphyrin IX is not symmetric with respect to the A and B rings, two possible products result depending on whether the Diels-Alder addition occurs in the A or B ring. On the other hand, protoporphyrins III and XIII are symmetric with respect to these rings, and therefore only one product results in each case regardless of the site of addition.

In the compounds of the invention, $R^2$ is preferably vinyl, but may also be a derivative thereof. The vinyl group in ring A or B is readily derivatized to other embodiments of $R^2$ by addition or oxidation. The addition or oxidation products can be further substituted if the added substituents are functional as leaving groups, for example, —Br may be substituted by —OH, —OR", —NH$_2$, —NHR", or —NR$_2$", etc., where R" is a hydrocarbon radical. For instance, one of the added substituents may be hydrogen and the other halo, hydroxy, lower alkoxy, amino, or an amide, sulfhydryl or an organosulfide or an additional hydrogen. The compounds of the invention include various groups as $R^2$ including substituents which provide additional porphyrin or porphyrin-related ring systems.

Thus, $R^2$ may be vinyl, —CHOR', —CHO, —COOR', —CH(OR') CH$_3$, —CH(OR')CH$_2$OR', —CH(SR') CH$_3$, —CH(NR')$_2$CH$_3$, —CH(CN) CH$_3$, —CH(COOR')CH$_3$, —CH(OOCR') CH$_3$, —CH(NR'COR')CH$_3$, —CH(CONR'$_2$) CH$_3$, —CH(halo)CH$_3$, or —CH(halo)CH$_2$(halo) wherein R' is H, or a hydrocarbon radical (1–6C) optionally substituted with a heteroatom substituent or wherein $R^2$ is an organic group of less than 12C resulting from direct or indirect derivatization of the vinyl group, or wherein $R^2$ is a group containing 1–3 tetrapyrrole-type nuclei.

As used herein, the term "alkyl" refers to a saturated straight or branched chain hydrocarbon which may, if it contains a sufficient number of carbon atoms, be cyclic or contain a cyclic portion. Typical examples are methyl, ethyl, t-butyl, cyclohexyl, and the like.

A "hydrocarbon radical" refers to a monovalent substituent containing only carbon and hydrogen which may be straight or branched chain, saturated or unsaturated, aromatic or nonaromatic or both, and cyclic or noncyclic. Thus, a hydrocarbon radical of 1–10C could include cyclopentylethyl, 2-pentenyl, 3-butynyl, 2,4-dimethylhexyl, and the like.

In some embodiments of the invention, the hydrocarbon radical may be substituted with a heteroatom-containing substituent. Such substituents include —OR, —NR$_2$, —SR, —COOR, —CONR$_2$, —OOCR, —NRCOR, —SOR, —SO$_2$R, —SO$_3$R, halo, —CN, and the like, wherein R is H or alkyl (1–6C). Cyclic amines include pyridyl, pyrimidyl, thiazolyl, quinolyl, and so forth. Thus, they may include single ring or fused ring systems and may contain additional heteroatoms.

Figure 14:
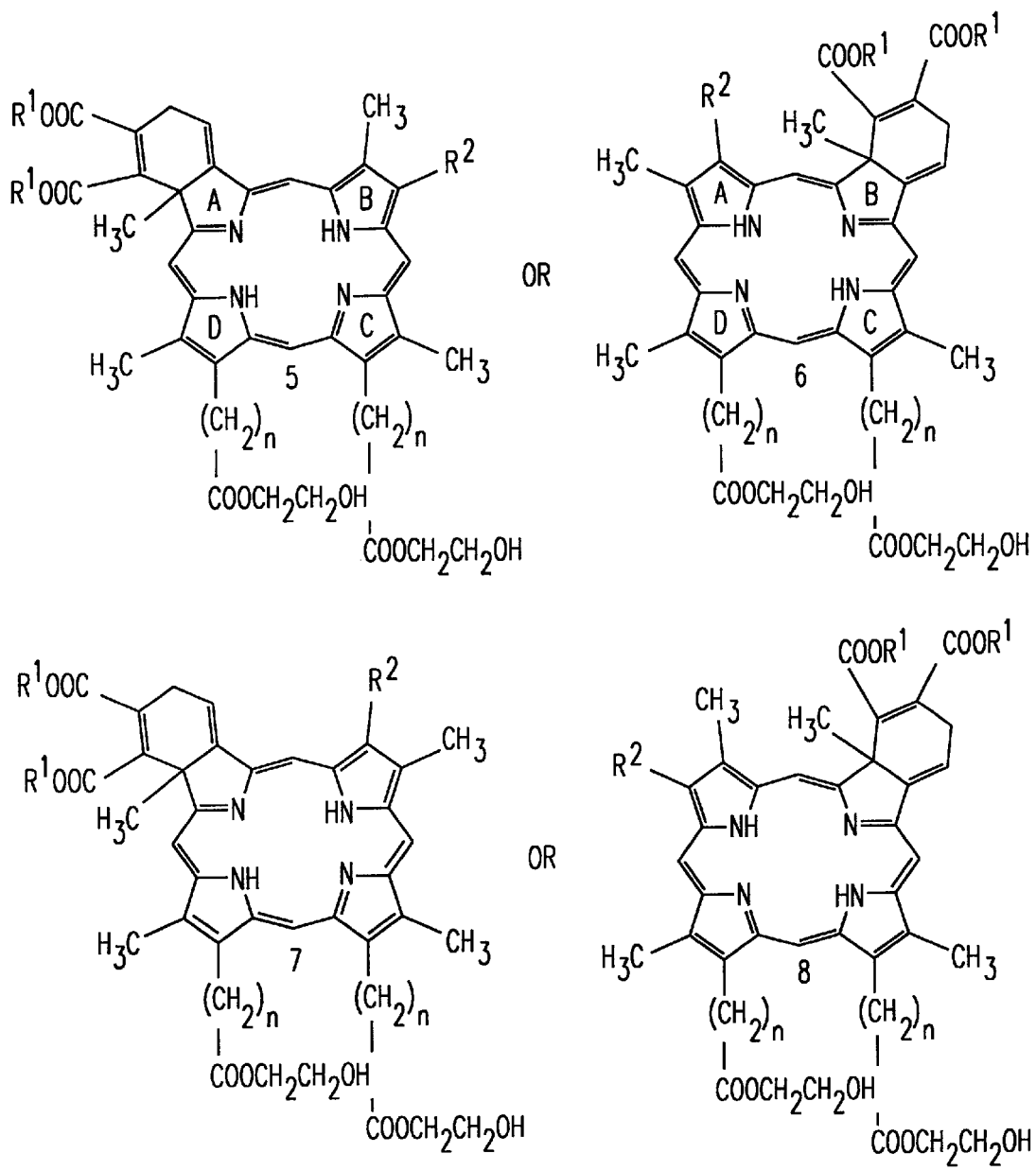
FIG. 14 shows the structures of the unrearranged Diels-Alder products that are precursors to the compounds of formulas 1–4.

It will be noted that the compounds of the invention contain at least one chiral center and thus may exist in various stereoisomeric forms. If desired, such stereoisomers, including enantiomers, may be separated using techniques standard in the art; however, racemic mixtures or mixtures containing more than one diastereomer may also be used. The compounds as indicated in formulas 1–4 and in FIG. 14, therefore, are representative of the individual optical isomers, enantiomers or diasteriomers as the case may be, as well as mixtures of these individual chiral isomers.

If desired, the compounds of the invention can be prepared in metallated forms by treating the tetrapyrrole-type nucleus with an appropriate ion such as magnesium ion, zinc ion, stannous ion and the like, to obtain a metal complex. The metal ion may also be a radiolabel. Generally, the metal ion is inserted using the appropriate salts under conditions standard in the art. For example, zinc ion can be introduced by treating the compound with zinc acetate in 1:1 methylene chloride:methanol.

The compounds may also contain label, including radioisotopes, chromophores, and fluorescent labels. Radioisotope labeling is generally useful when the compounds are to be followed in vivo or used to label specific moieties. Useful cationic moieties that are radioisotopes include technetium, gallium and indium. In addition, radioisotopes of heteroatoms, such as $^{131}$I or $^{32}$P, in the molecule itself, or inclusion of $^{14}$C may be used to label the molecule.

As further described in the BPD-related patents set forth above, the compounds of the invention may be coupled, if desired, to a targeting agent which will direct the molecule to a specific tissue or organ. Such targeting agents include antibodies, receptors, receptor-ligands and the like. Linkage of the targeting agent to the compound is conducted using standard techniques. By a "conjugated form" is meant a compound of formulas 1–4 coupled to a targeting agent, as above described.

Preferred embodiments of the compounds of formulas 1–4 and their 1,4-diene isomers include those wherein both n equal 2, or those wherein both R$^1$ are ethyl or methyl, preferably methyl, and those wherein R$^2$ is vinyl. Particularly preferred are compounds of the formula

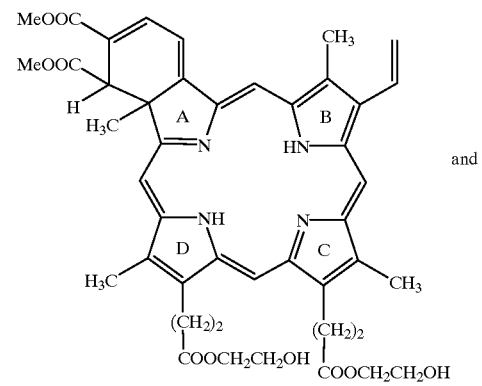

A-EA6 and

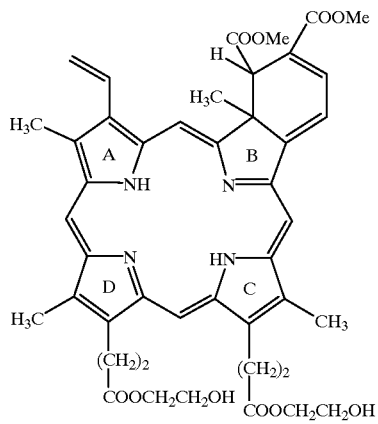

B-EA6

Both A-EA6 and B-EA6 are effective photosensitizers; it appears that A-EA6 is the easier to formulate.

The various forms of the compounds of the invention can be used in the photodynamic therapy techniques generally known in the art. As set forth in the Background section above, photodynamic therapy can be conducted using a plethora of protocols and for a variety of indications. In addition, compounds of this type exhibit pharmacological activity in the absence of light in some instances. Standard pharmaceutical compositions, including liposomal compositions as preferred, are used as desired in such applications.

The following examples are intended to illustrate but not to limit the invention. While the Examples illustrate and demonstrate the surprising pharmacokinetic properties of two members of the species of the invention, A-EA6 and B-EA6, it is expected that the remaining compounds described by formulas 1–4 and their 1,4-diene isomers will have similar variations in these properties. Hence, the small class of compounds contained in the present invention offers valuable additions to the repertoire of photodynamic agents useful in treating the various conditions to which this therapy has been directed.

EXAMPLE 1

Preparation of Two Forms of EA6

A. To prepare B-EA6, the starting material is BPD-DB as the dimethyl ester—i.e., BPD-DB as shown in FIG. 1 wherein R$^1$ and R$^2$ are both COOMe an R" is vinyl.

To 2.0 g (2.7 mM) BPD-DB in 50 mL ethylene glycol and 100 mL dichloromethane was added 1.0 mL sulfiuric acid. The reaction was stirred for 18 hr. at room temperature. Then the reaction was added to a stirring mixture of 100 mL 5% aqueous ammonium acetate and 100 mL dichloromethane. The organic layer was isolated and then washed twice with 50 mL water. The solvent was removed by rotary evaporation. The dark green residue was then chromatographed on 75 g alumina (deactivated with 5% water) and eluted with a gradient of 0.5%–5.0% methanol in dichloromethane. The solvent from the fractions containing product was then removed by rotary evaporation. The residue was dried in vacuo overnight to provide 2.02 g (89%) of the analytically pure green sold title compound.

B. In a manner similar to that set forth in paragraph A, but substituting BPD-DA for BPD-DB, the isomeric form, A-EA6 was prepared.

EXAMPLE 2

Comparison of Uptake and Release of B-EA6 and BPD-MA by L1210 Cells

Figure 2:
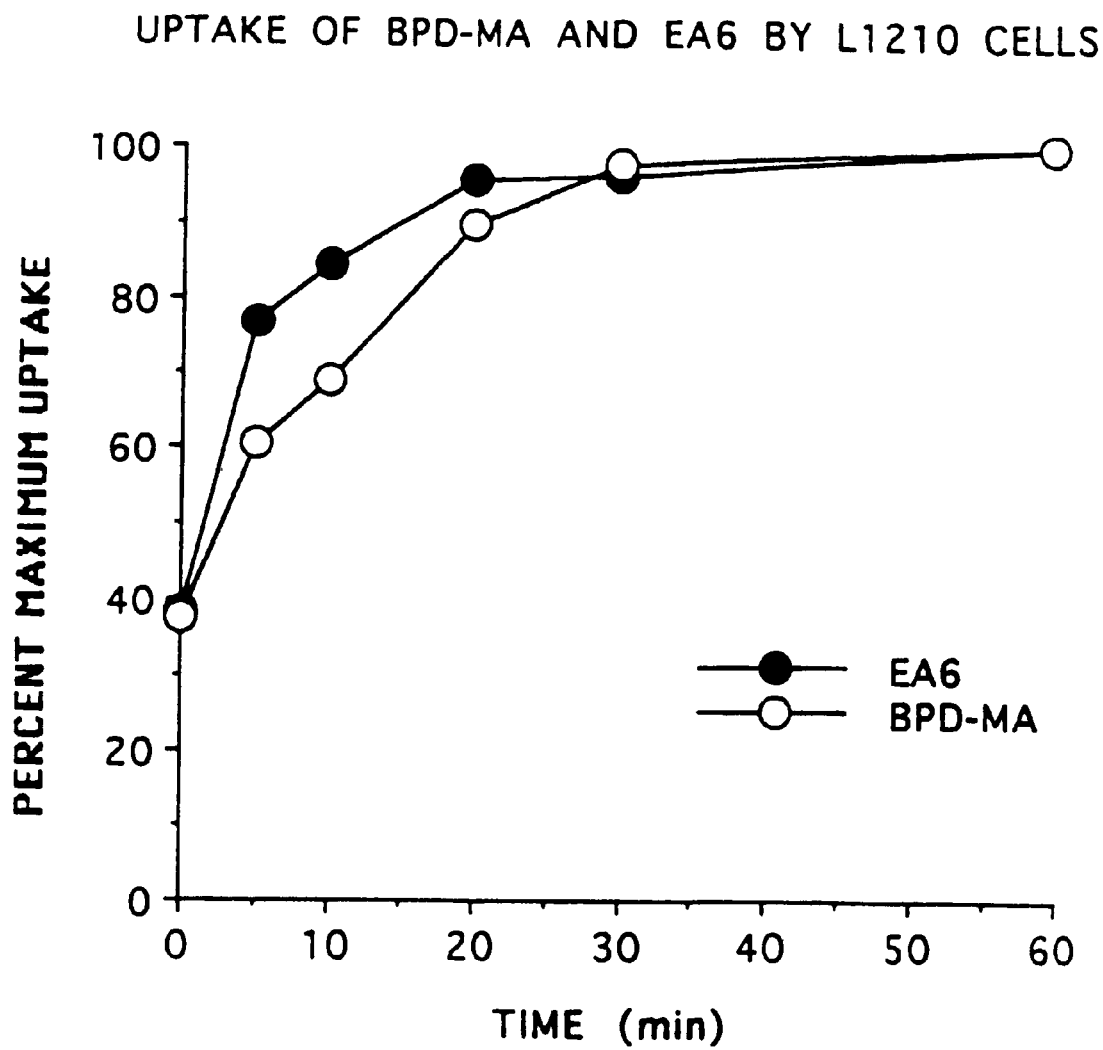
FIG. 2 shows the kinetics of uptake of B-EA6 by L1210 cells.

BPD-MA or B-EA6 were incubated at 3μg/ml in the presence of 10% fetal bovine serum with $10^7$/mL of L1210 cells, a murine leukemia cell line. Intracellular content of the photosensitizers was measured by fluorescence of cell lysates at various times. The maximum concentration reached was 145.9 ng/$10^6$ cells for B-EA6 and 149.5 ng/$10^6$ cells for BPD-MA. The time course of uptake is shown in FIG. 2 as a percentage of cell content at 60 min by which time uptake had reached a maximum in both cases. As shown, B-EA6 is taken up more rapidly and reaches 80% of its maximum concentration after only 5 min and reached its maximum uptake within 15 min.

Figure 3:
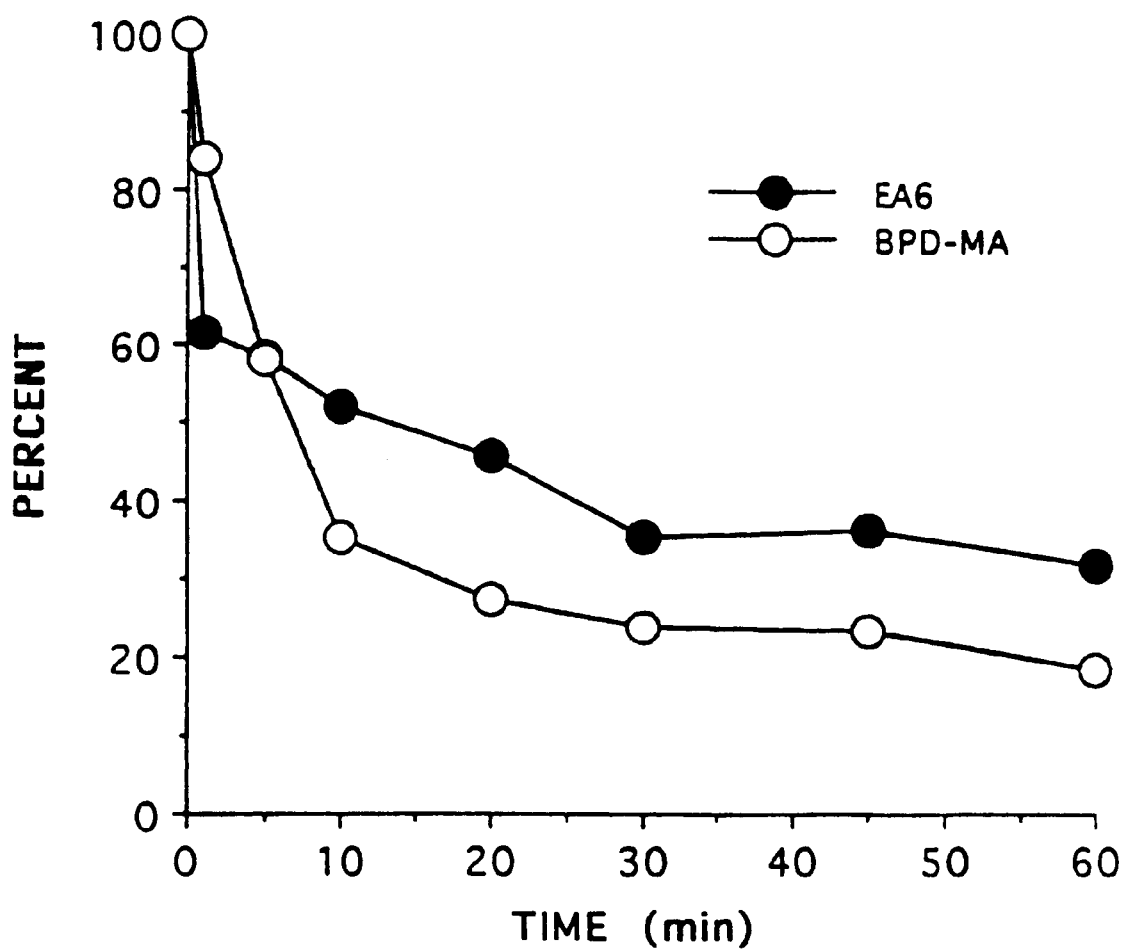
FIG. 3 shows the kinetics of release of B-EA6 by L1210 cells.
Figure 4A:
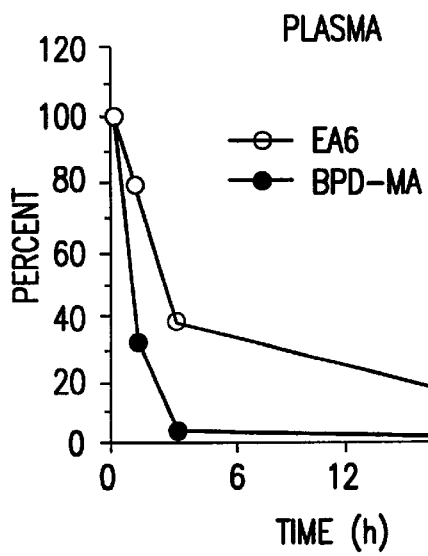
FIG. 4 shows a graphic depiction of the pharmacokinetics of B-EA6 in vivo.
Figure 4B:
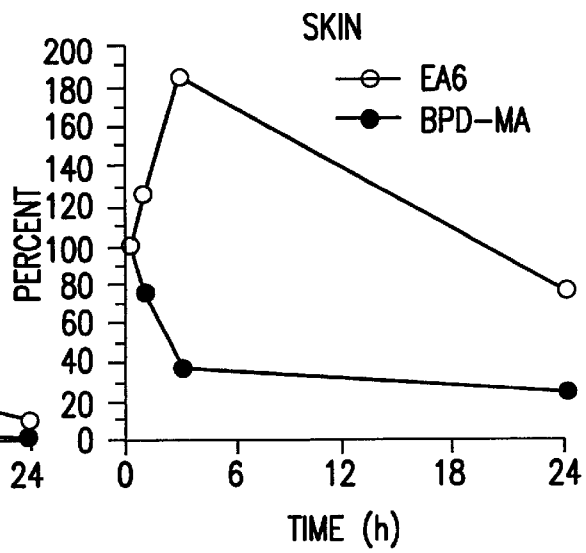
Figure 4C:
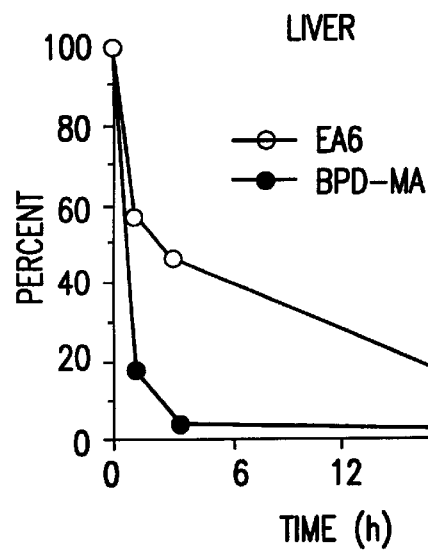
Figure 4D:
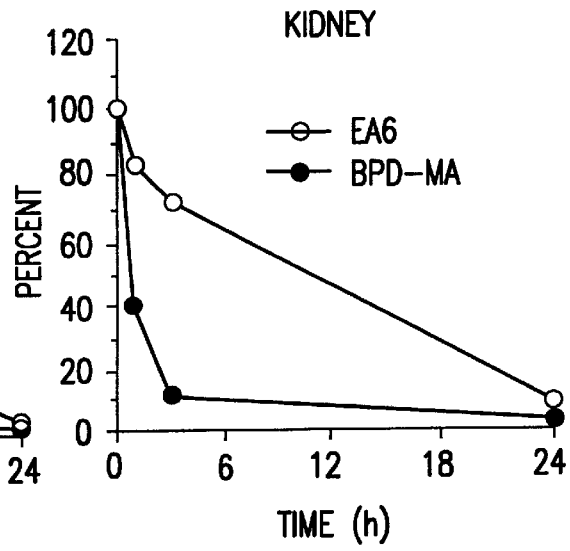

The kinetics of release of these drugs from L1210 cells was measured by preloading the cells at 3μg/ml for 1 hr and then placing the cells in drug-free medium containing 10% fetal bovine serum. Remaining intracellular drug content was measured at various time points by lysing the cells and measuring fluorescence. As shown in FIG. 3 (again as a percent of starting intracellular content), BPD-MA and B-EA6 showed different kinetics of release. Initial release of B-EA6 was much more rapid, but release was more complete in the case of BPD-MA.

It was unexpected that the in vitro pharmacokinetics of B-EA6 were more rapid than those of BPD-MA. While the higher retention of B-EA6 could be attributed to its increased size as compared to BPD-MA, the faster transfer through the cellular membrane was unexpected.

EXAMPLE 3

Comparison of In Vivo Pharmacokinetics

Either BPD-MA or B-EA6 was administered by intravenous injection into DBA/2 mice at a dose of 4 mg/kg using 3 mice per time point. The drug content of plasma, skin, liver and kidney was determined by fluorescence in the tissue extracts. FIG. 4 shows the results plotted as a percentage of the concentration in the relevant tissue 15 min postinjection. As seen in FIG. 4, neither BPD-MA nor B-EA6 accumulated in plasma, liver or kidney; however, BPD-MA accumulated in skin within the first 3 hr; B-EA6 does not.

The more rapid accumulation of B-EA6 as compared to BPD-MA, as here confirmed in vivo by more rapid clearance from all tissues, constitutes an advantage. The treatment with light can be carried out soon after injection of the photosensitizer and due to the rapid clearance, no prolonged skin or eye photosensitivity will be exhibited. Thus, the subjects treated can resume normal lives without special precautions such as avoiding bright light and wearing dark eyeglasses.

The half-life of B-EA6 and BPD-MA in various tissues was then computed in the time-frame min-3 hr and the results are shown in Table 1:

TABLE 1

Tissue Half-Lives of B-EA6 and BPD-MA

| Tissue | T½* (15 min–3 hours) | |
|---|---|---|
|  | B-EA6 | BPD-MA |
| Liver | 0.6 | 2.4 |
| Spleen | 0.8 | 10.9 |
| Kidney | 0.8 | 5.6 |
| Skin | 1.9 | 0** |
| Muscle | 11.1 | ND† |
| Plasma | 0.6 | 2.0 |

*shown in hours
**BPD-MA concentration in the skin increased for up to 3 hr
†ND = not determined The half-life of BPD-MA in this time-frame could not be computed in skin since its concentration increased during the 3 hr period. As shown in Table 1, generally, B-EA6 has a much shorter half-life than BPD-MA in most tissues. The lack of accumulation of B-EA6 in normal skin as compared to BPD-MA was unexpected, and indicates more rapid clearance than that of BPD-MA. As set forth above, this is advantageous as skin photosensitivity is the only recognized side effect of photodynamic therapy utilizing photosensitizers.

The pharmacokinetics were also determined using an in vivo mouse tumor model. Groups of 10 DBA/2 mice containing M1 rhabdomyosarcoma tumors were injected intravenously with a liposomal formulation of BPD-MA at various dosages of 0.75–1.5 mg/kg. The tumors were irradiated with 690 nm laser light at 50 or 150 J/cm² at various times after injection. The results, as shown in Table 2, were determined in terms of the percentage of mice in each group that were tumor-free on day 7 after injection.

TABLE 2

Results of Bioassay

| PDT Conditions | | | | |
|---|---|---|---|---|
| Drug** Dose | Time post IV | Light*** dose | Percent Tumor Free on Day 7* | |
| (mg/kg) | (min) | (J/cm²) | BPD-MA | B-EA6 |
| 0.75 | 15 | 50 | (4/5) | 50% |
|  | 30 | 50 | 70% | 0% |
| 1.0 | 15 | 50 | 100% | 90% |
|  | 30 | 50 | 90% | 0% |
| 1.5 | 180 | 150 | 70% | 0% |

*tumor model = MI tumor in DBA/2 mice - each PDT condition was tested in 10 animals
**the drugs were liposomally formulated and injected intravenously
***690 nm laser light.

As shown in Table 2, BPD-MA treated mice showed substantial survival rates when postinjection times ranged from 15–180 min. On the other hand, B-EA6 treated mice showed no response at 30 min or 180 min; however, significant responses were obtained when irradiation was supplied after only 15 min.

These data demonstrate that PDT using B-EA6 will be effective in early treatment with light. The lack of effect of later times postinjection indicates, again, rapid clearance of B-EA6 which is advantageous for the reasons set forth above.

EXAMPLE 4

Determination of $LD_{50}$ With and Without Serum

Either B-EA6 or BPD-MA was incubated for 1 hr with L1210 cells at a range of concentrations and exposed to 9 J/cm² broad spectrum light. This determination was made in the absence of serum and in the presence of 10% serum. The results are shown in Table 3.

TABLE 3

| | $LD_{50}$ Values | |
|---|---|---|
| | No serum | 10% serum |
| BPD-MA | 3.7 ng/ml | 54.0 ng/ml |
| B-EA6 | 4.7 ng/ml | 19.7 ng/ml |

As shown, BPD-MA and B-EA6 have comparable $LD_{50}$ values in the absence of serum; however, in the presence of serum, B-EA6 shows a substantially better retention of effectiveness.

In most instances, the presence of serum greatly reduces the photoactivity of agents used in PDT, such as BPD-MA. Surprisingly, B-EA6 shows more affinity for cell membranes than for plasma components and is thus very slightly affected by the presence of serum in the cellular environment. Thus, in vivo, its activity may be higher than that of BPD-MA and other compounds of this family.

EXAMPLE 5

In Vitro Efficacy of B-EA6

The ability of B-EA6 to exert a cytotoxic effect on L1210 cells in vitro was further tested by incubating the cells with B-EA6 at various concentrations for 1 hr in the absence of serum. After excess drug was removed, the cells were exposed to 9 J/cm² broad spectrum light (380–750 nm) and cell survival was determined by the MTT assay (Mosmann, T. et al. *J Immunol Meth* (1983) 65:55–63). The percentage of killed cells was calculated in reference to survival of cells exposed to light only. At a concentration of approximately 7 ng/ml, 80% of the cells were killed; at 15 ng/ml, almost 100% of the cells did not survive. As stated above, the $LD_{50}$ for B-EA6 is approximately 4.7 ng/ml.

The somewhat lower effect of B-EA6 as compared to BPD-MA in vitro makes even more unexpected the comparatively higher activity of B-EA6 as compared to BPD-MA in vivo in the presence of serum as demonstrated in Example 4.

EXAMPLE 6

Selectivity of B-EA6 for Tumor Cells

Figure 5:
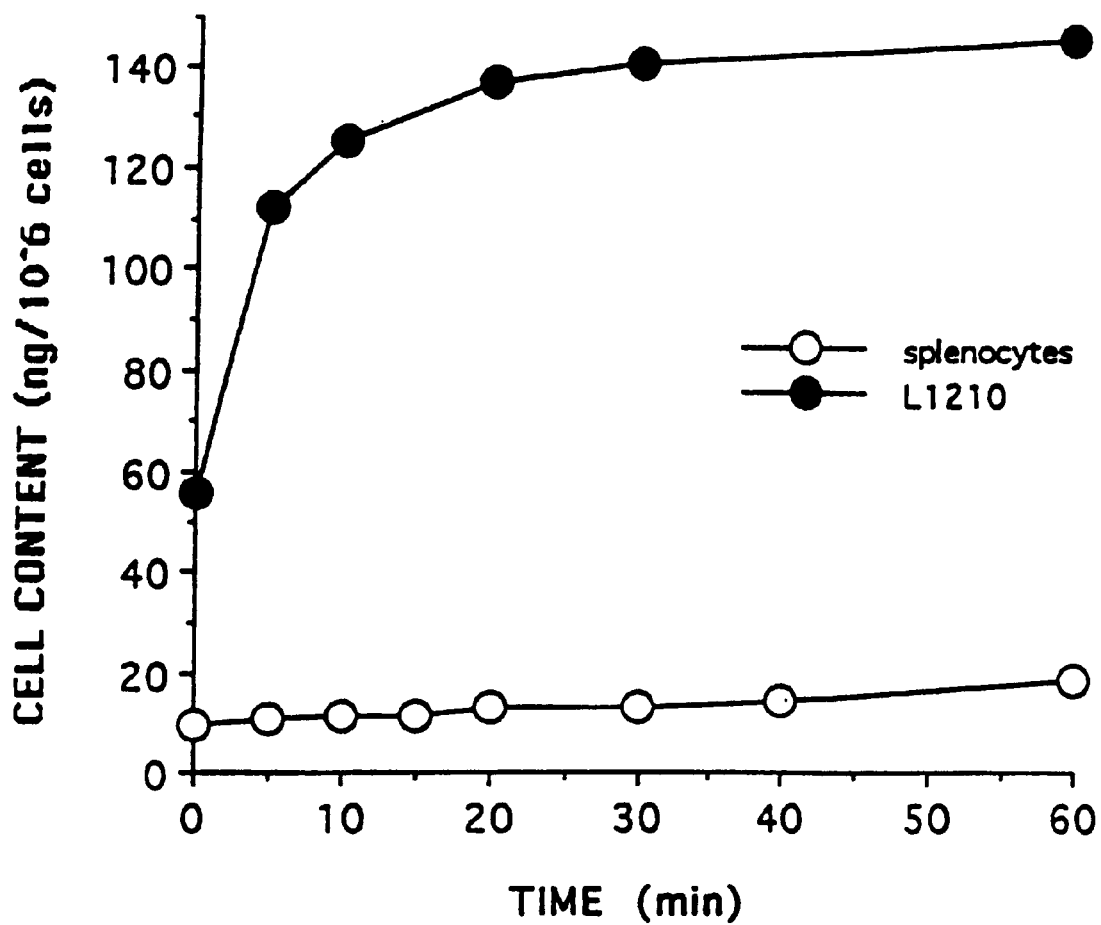
FIG. 5 shows a comparison of the kinetics of uptake of B-EA6 by normal splenocytes and L1210 cells.

The ability of L1210 cells to accumulate B-EA6 was compared to the ability of splenocytes to do so. B-EA6 at 3 μg/ml was incubated with each cell type and the cell content of B-EA6 was determined by fluorescence in cell lysates. FIG. 5 shows a comparison of uptake for the two cell types in ng/$10^6$ cells. As shown, L1210 cells were able to take up approximately 140 ng/$10^6$ cells reaching this value after approximately 20 min. Splenocytes, on the other hand, accumulated less than 20 ng/$10^6$ cells after an hour of incubation.

DBA/2 mice bearing M1 (rhabdomyosarcoma) tumor, grown subcutaneously in their flanks, were used as a model to show that B-EA6 demonstrated selectivity for tumors. Mice were administered 0.75 mg/kg of B-EA6 in a liposomal formulation intravenously. After 15 min, a 1 cm area which included a 5 mm diameter tumor was exposed to 50 J/cm² of 70 mW light of 690 nm wavelength from an argon-pumped dye laser. The exposure effectively eliminated the tumor, but did not affect the surrounding normal skin. Thus, B-EA6 demonstrates tumor specificity.

EXAMPLE 7

Immunomodulation by B-EA6

Balb/C mice (5–8 mice per group) were tested using the delayed skin photosensitivity assay also called the contact hypersensitivity (CHS) assay. The mice were painted in the flank with the sensitizing agent dinitrofluorobenzene (DNFB) and 5 days later, one ear is challenged with DNFB, while the other serves as a control. The swelling is an indicator of immune response. Mice were injected intravenously with 1 mg/kg liposomal B-EA6 and either irradiated with 15 J/cm² light over the whole body or exposed to ambient light. The ability of this treatment to prevent the immune response as demonstrated by inhibition of ear swelling was determined. The results showed that administering B-EA6 combined with either after irradiation with 15 J/cm² whole body light or with ambient light decreased swelling in the test ear as compared to untreated mice. The swelling in both cases was only approximately 60% of the that shown in mice without treatment.

In an additional assay to determine immunomodulation, murine peritoneal macrophages were isolated, purified and activated by recombinant interferon-γ (100 U/ml). The activated cells were incubated for 1 hr at 37° C. with B-EA6 at a range of concentrations and then exposed to 690 nm LED light at 5 J/cm². Expression levels of MHC I, MHC II, CD54, CD80 and CD86 were determined 24 hr later using FITC conjugated antibodies and a cell sorter. The results are shown in Table 4 for B-EA6 at 0.5 ng/ml in comparison to similar experiments using BPD-MA at 2.5 ng/ml.

TABLE 4

Effect of Low-Dose PDT with B-EA6 on Expression Levels of Cell Surface Antigens by Murine Peritoneal Macrophages

| Compound | MHC Class I | MHC Class II | CD54 (ICAM-1) | CD80 (B7-1) | CD86 (B7-2) |
|---|---|---|---|---|---|
| BPD-MA (2.5 ng/ml) | 99.1 ± 4.3% | 79.3 ± 10.1% | 105.4 ± 3.0% | 93.5% | 99.2% |
| BPD-B-EA6 (0.5 ng/ml) | 100.4% | 71.8% | 106.9% | 102.3% | 92.2% |

The results in the table are given as a percent of expression as compared to cells treated with light only. As shown, BPD-MA and B-EA6 were both able to reduce expression of MHC II, but not the remaining surface markers. Thus, although B-EA6 has advantageous pharmacokinetics, it retains the immunomodulatory activity of BPD-MA and other compounds of this group.

EXAMPLE 8

Effect of B-EA6 in an Arthritis Model

Figure 6A:
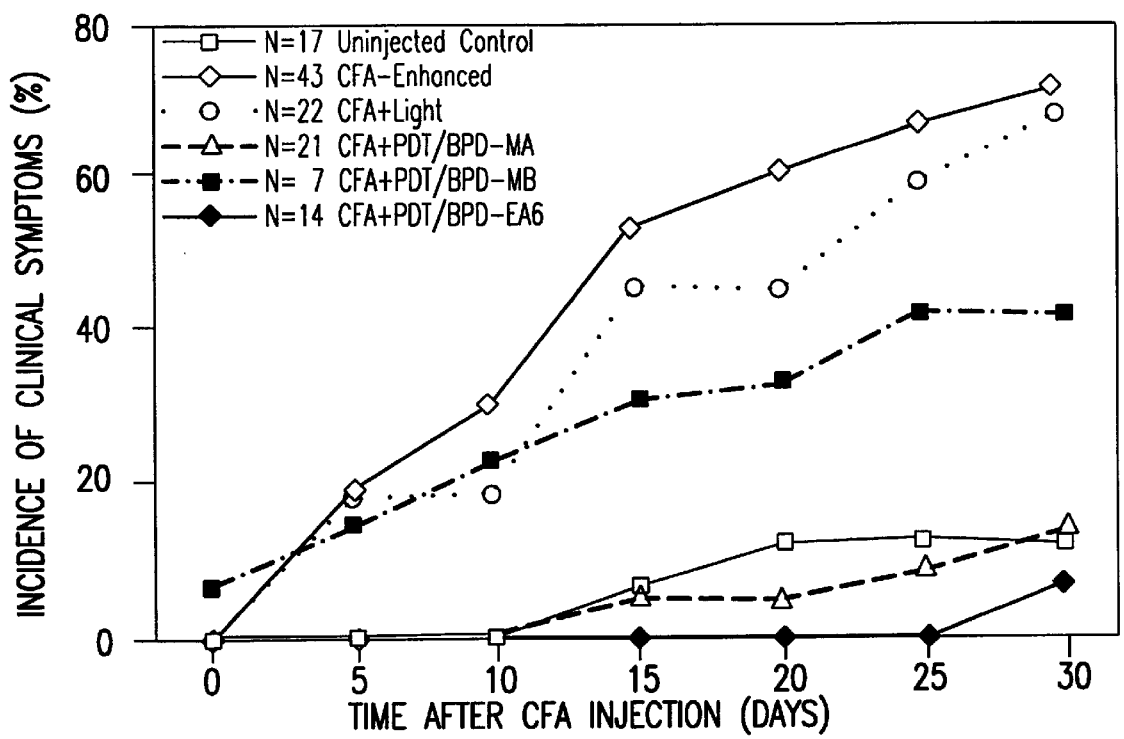
FIG. 6 shows the time course of PDT using B-EA6 in mice as compared to mice treated with BPD-MA and BPD-MB.
Figure 6B:
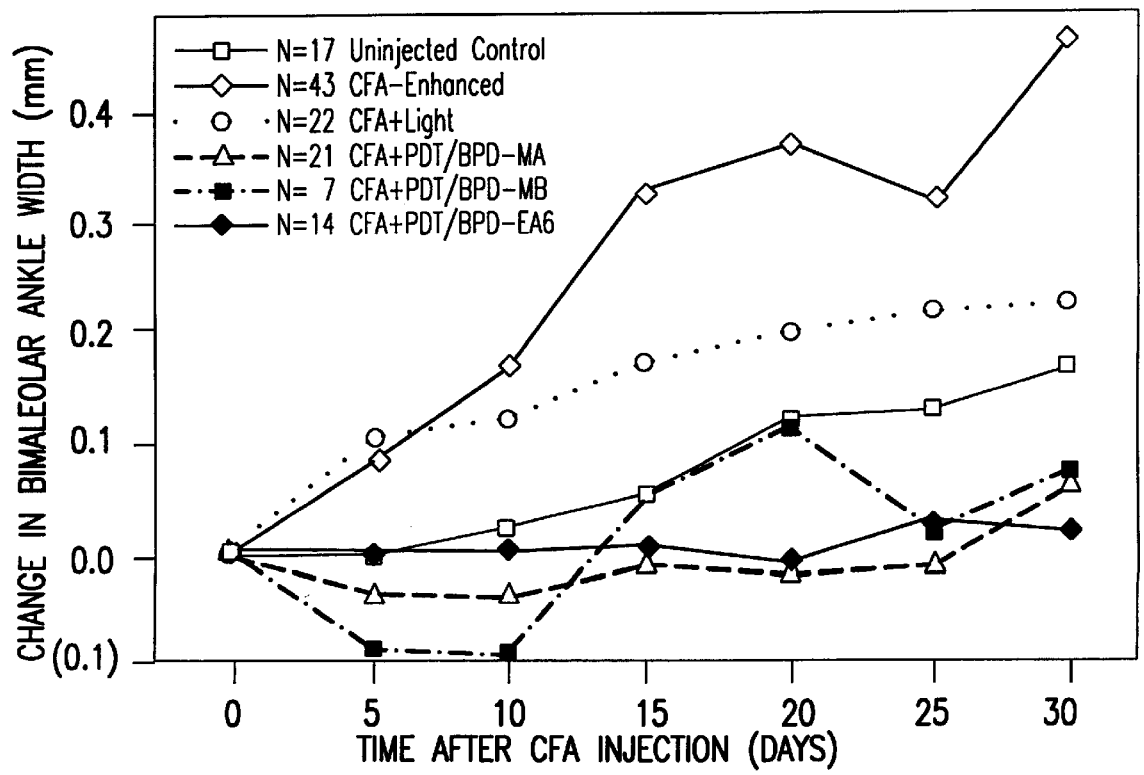

MRL-Ipr mice spontaneously develop arthritis; this was enhanced by intradermal injection of Freund's Adjuvant. Various numbers of MRL-Ipr mice were treated with PDT on days 0, 10, and 20 after injection of the adjuvant. PDT consisted of 0.5 mg/kg liposomal B-EA6 injected intravenously followed by exposure of the ventral part of the mice to red (560–900 nm) light at 80 J/cm² at 1 hr post-B-EA6 injection. The mice were observed and symptoms scored every 5 days for 30 days. The results are shown in FIG. 6 in comparison to mice similarly treated with BPD-MA and BPD-MB. As shown in FIG. 6, whether measured by the incidence of clinical symptoms (i.e., the percentage of mice exhibiting these symptoms) or by the change in bimaleolar ankle width in millimeters, B-EA6 (shown as solid circles) was effective in preventing the sequellae of adjuvant injection.

Again, the retention of immunomodulatory activity of B-EA6 is demonstrated.

EXAMPLE 9

Effect of B-EA6 on Microvasculature

The mouse cremaster muscle model was used. B-EA6 was administered intravenously at 2 mg/kg and starting at 5 and 15 min postinjection, surgically exposed arterioles and venules were iaradiated with light at an intensity of 25 J/cm² per 5 min beginning at 5 min and 15 min after injection of the B-EA6. The vessels were measured as red blood column diameter as a percentage of controls.

Figure 7A:
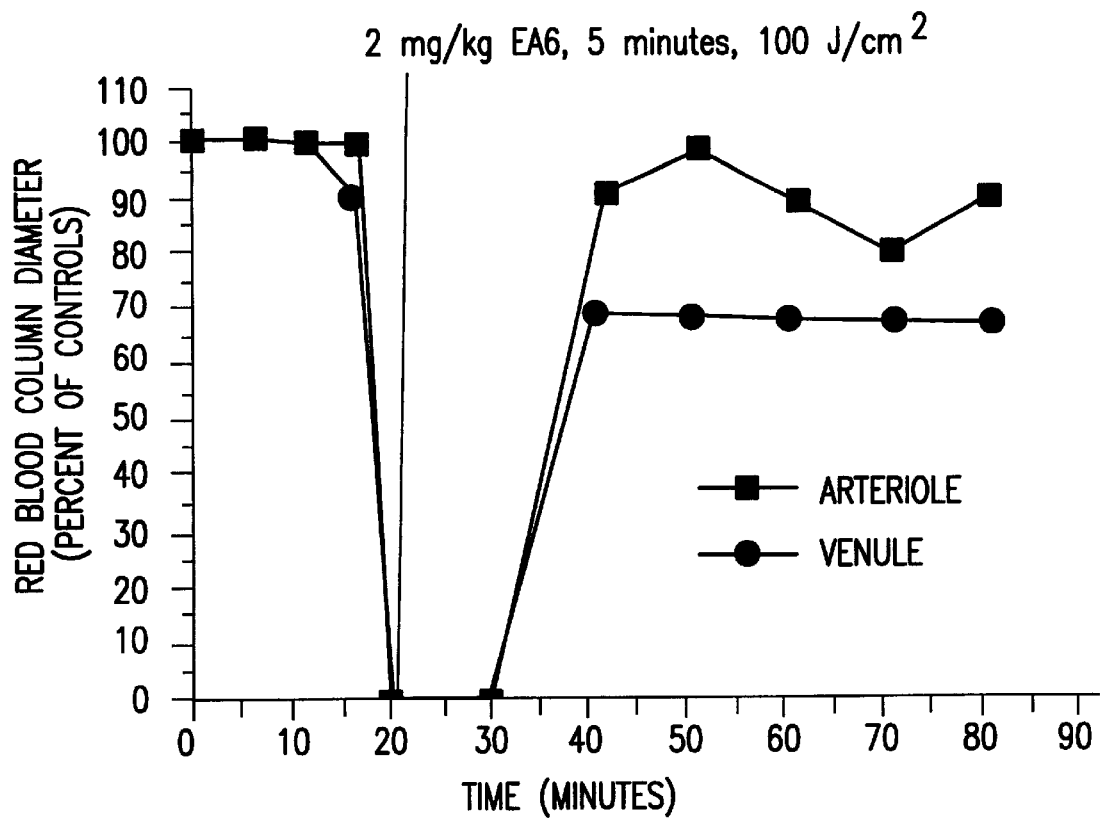
FIG. 7 shows the effect of B-EA6 on microvasculature in mice.
Figure 7B:
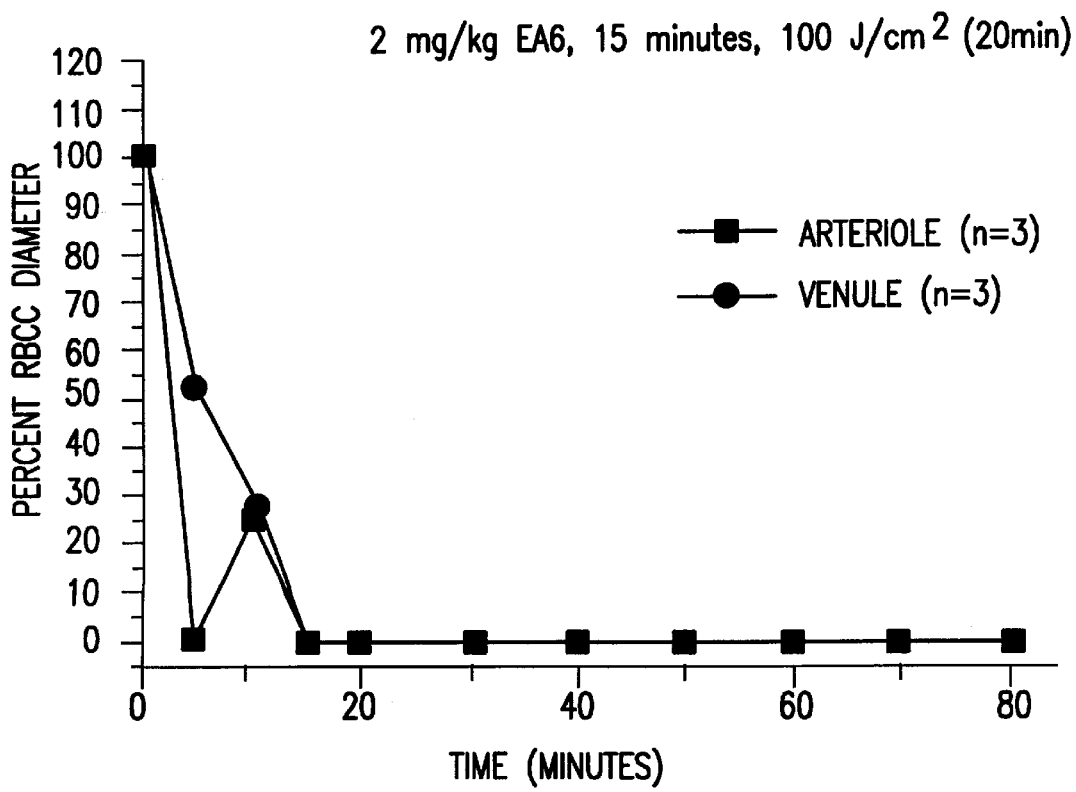

The results are shown in FIG. 7. While transient vessel closure could be obtained when irradiation was started at 5 min, permanent closure was obtained when radiation was started after 15 min.

The enhanced capacity of B-EA6 to constrict or occlude vasculature, as demonstrated in this Example, in combination with more rapid pharmacokinetics, make B-EA6 particularly advantageous in treating neovascular diseases in the eye.

EXAMPLE 10

Absorption Spectrum of B-EA6

Figure 8A:
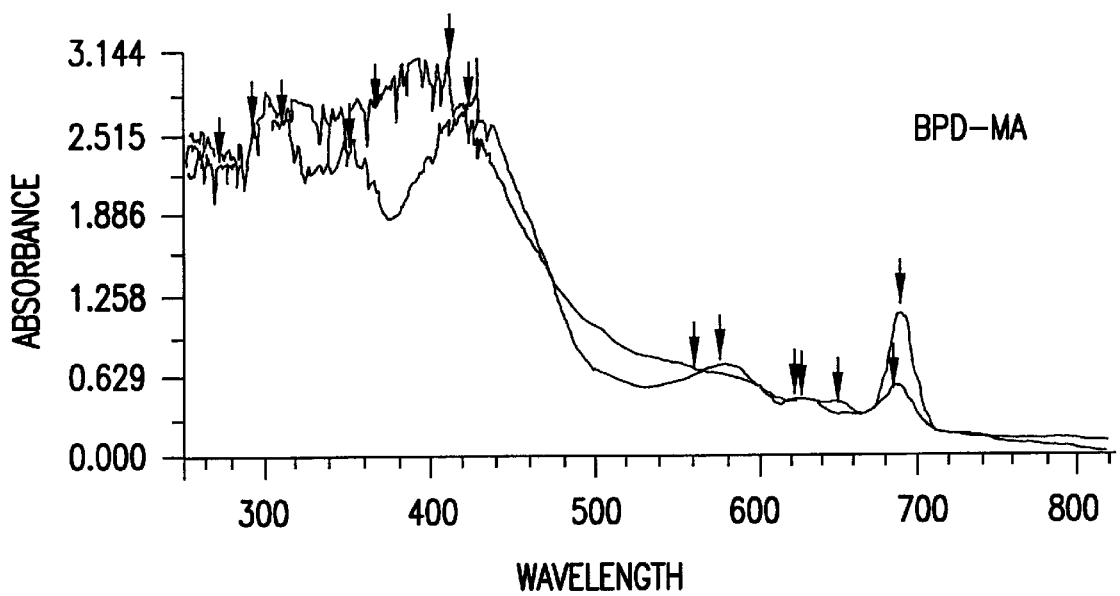
FIG. 8 shows a comparison of the spectra in plasma of BPD-MA and B-EA6.
Figure 8B:
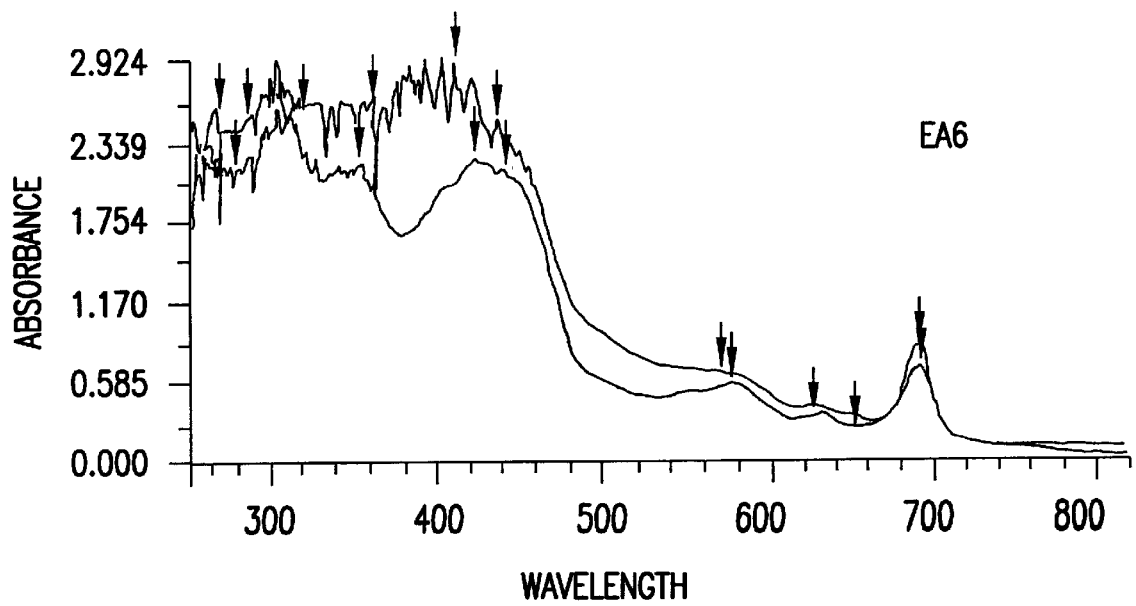

BPD-MA and B-EA6 have similar absorption spectra in plasma before and after 4-hr exposure to fluorescent (380–750 nm) light. A comparison of these spectra is shown in FIG. 8. The similarity of the spectrum of B-EA6 to the spectrum of BPD-MA is advantageous since the use of BPD-MA as a therapeutic agent useful in PDT is well developed. The similarity in their spectra indicates that the same light sources can be used for B-EA6 as are successful in treatment with BPD-MA.

EXAMPLE 11

In Vitro Cytotoxicity of A-EA6

Figure 9A:
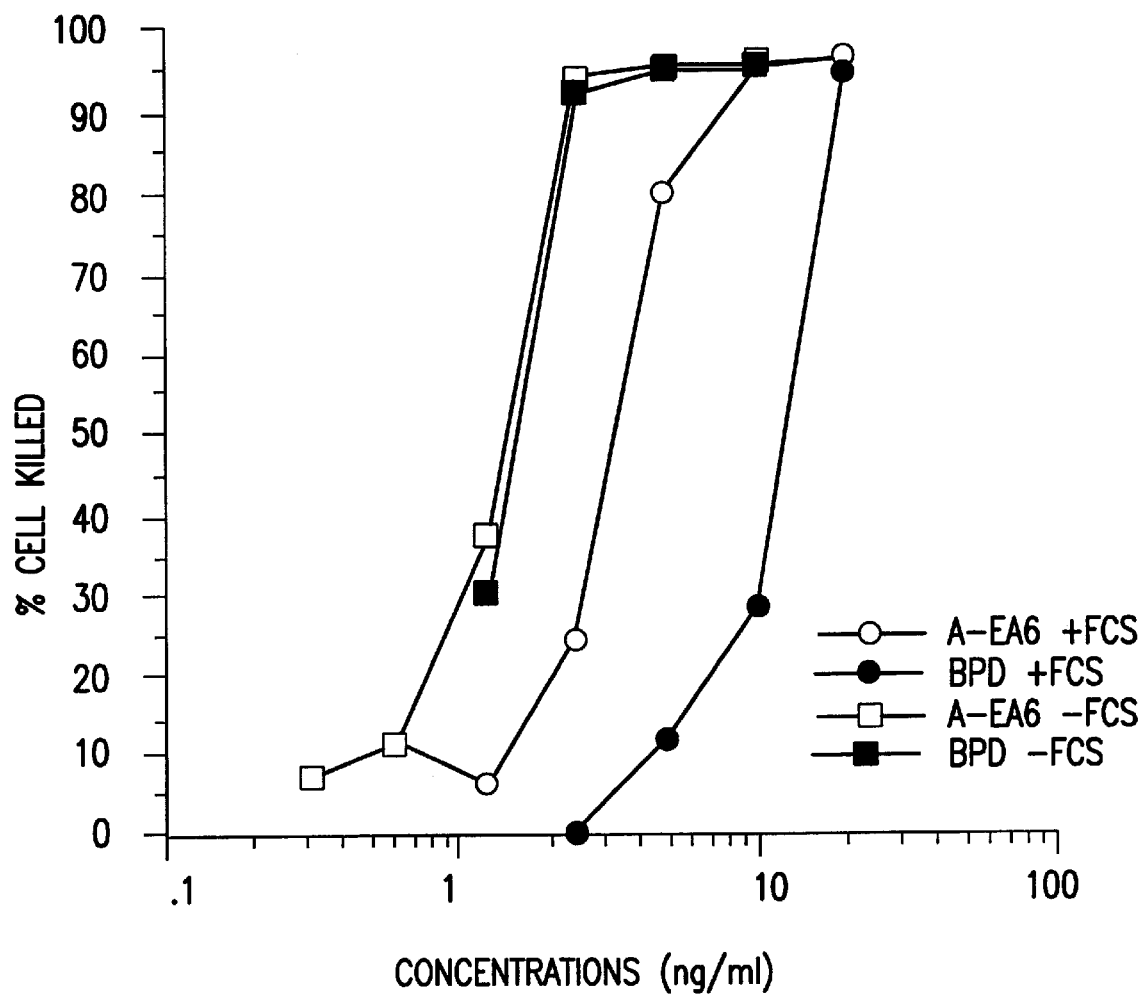
FIGS. 9A and 9B show the cytotoxic effect of photodynamic treatment using A-EA6 in comparison with BPD-MA in L1210 cells and in dendritic cells.

In a manner similar to that set forth in Example 5, the cytotoxicity of A-EA6 in vitro on two different cell lines was tested and compared with BPD-MA. Either L1210 cells or the dendritic cell line D2SC/1 was incubated for one hour at 37° C. with either A-EA6 or BPD-MA. After removal of excess drug, the cells were exposed to 690 nm light at 5 J/cm² light. Cell survival was determined 18–24 hours later using the MTT colorimetric assay described in Example 5. Percent cells killed was calculated by reference to cells exposed to light only. As shown in FIG. 9A, A-EA6 showed comparable cytotoxicity to BPD-MA with respect to L1210 cells in the absence of serum but was markedly more toxic in the presence of serum than BPD-MA. The open circles represent A-EA6 plus serum; the closed circles represent BPD-MA plus serum; open squares represent A-EA6 in the absence of serum; and closed squares represent BPD-MA in the absence of serum.

Figure 9B:
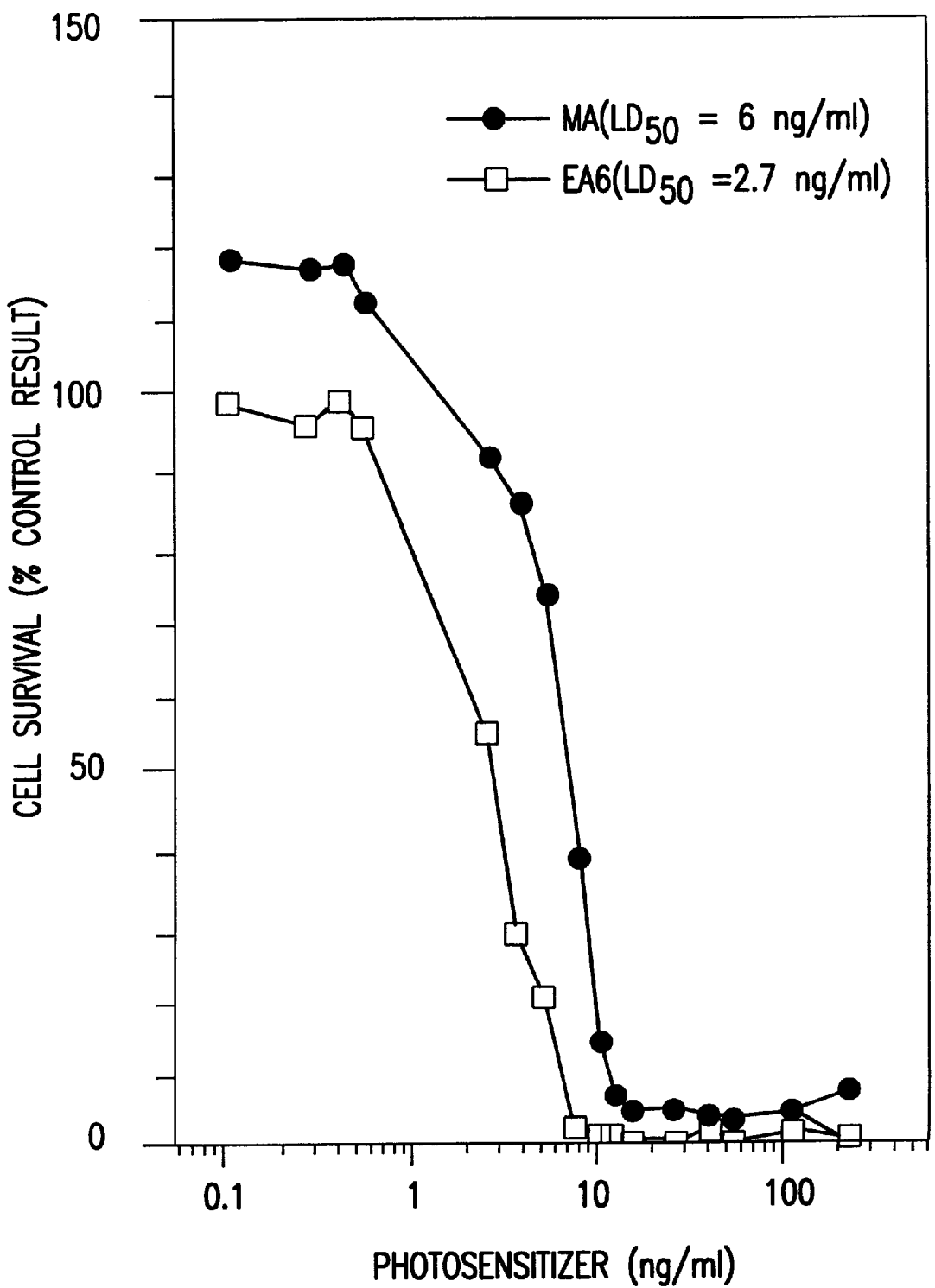

As shown in FIG. 9B, in dendritic cells where BPD-MA has an $LD_{50}$ of 6 ng/ml and A-EA6 has an $LD_{50}$ of 2.7 ng/ml, A-EA6 was toxic at lower concentrations than BPD-MA in the presence of 5% fetal calf serum. In FIG. 9B, closed circles represent BPD-MA and open squares represent A-EA6.

Figure 10:
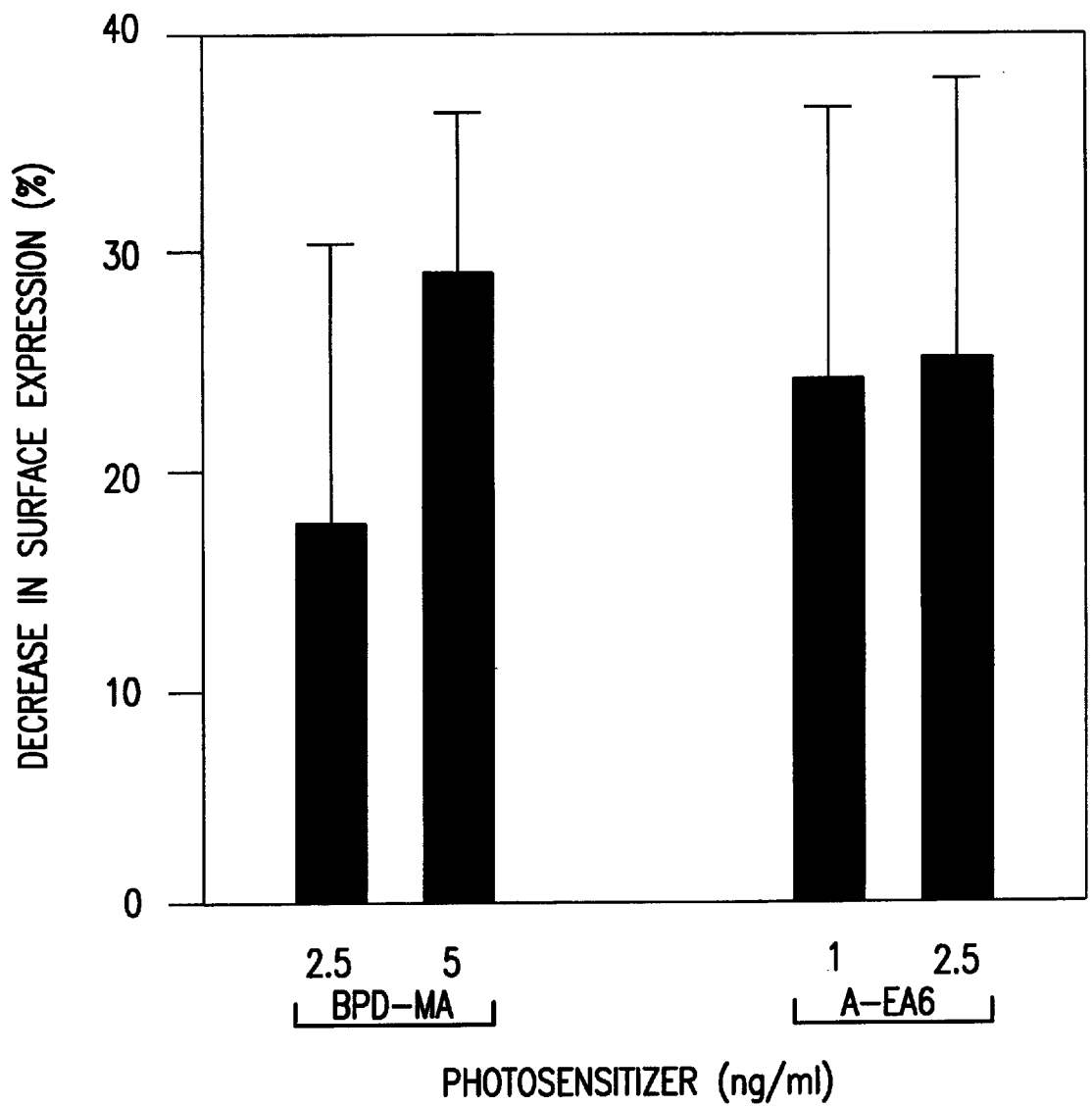
FIG. 10 shows the comparative effects of A-EA6 and BPD-MA in decreasing the surface expression of MHC I receptors.

In a similar determination, but measuring MHC I receptors rather than cytotoxicity, A-EA6 was effective in decreasing expression of these receptors at lower concentrations. In this determination, dendritic cells were incubated for 1 hour at a drug concentration less than its $LD_{50}$; 2.5 ng/ml and 5 ng/ml for BPD-MA and 1 ng/ml and 2.5 ng/ml for A-EA6. The cells were treated with 690 nm light at 5 J/cm² and then labeled with the appropriate antibody 3 hours post-treatment and assessed by flow cytometry. The results were measured as the percent of the mean channel fluorescence intensity for light-treated control cells. These results are shown in FIG. 10; BPD-MA gave an 18% and a 29% reduction, respectively, at 2.5 ng/ml and 5 ng/ml; A-EA6 lowered the channel fluorescence by approximately 25% at both 1 ng/ml and 2.5 ng/ml concentrations.

EXAMPLE 12

Effect of A-EA6 on Intracellular Signaling

Figure 11A:
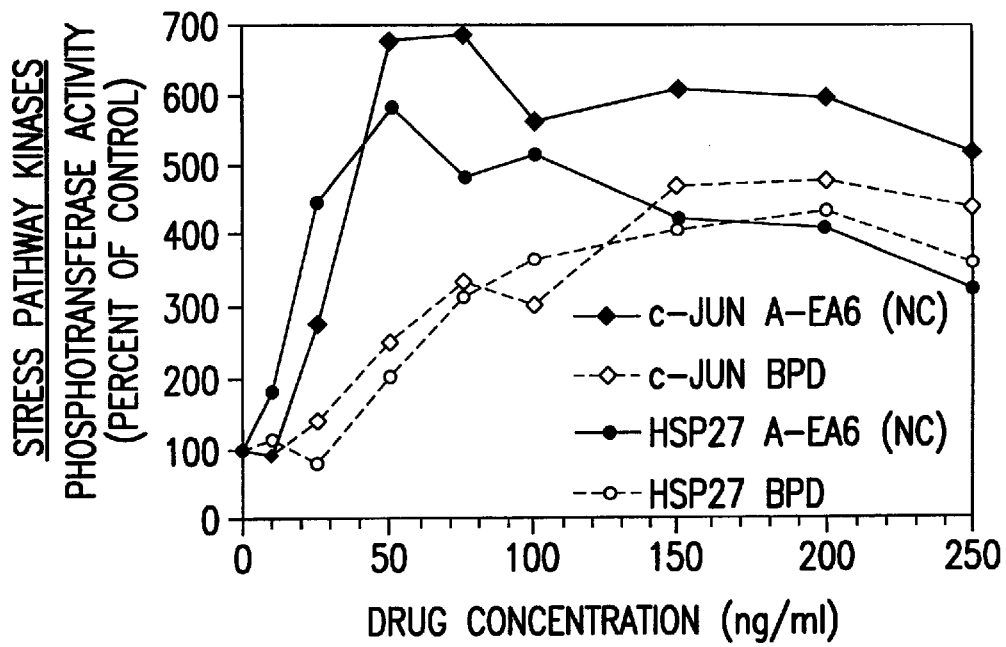
FIG. 11 shows the effect of photodynamic therapy using A-EA6 and BPD-MA on stress and mitogenic pathway kinases in HL60 cells.
Figure 11B:
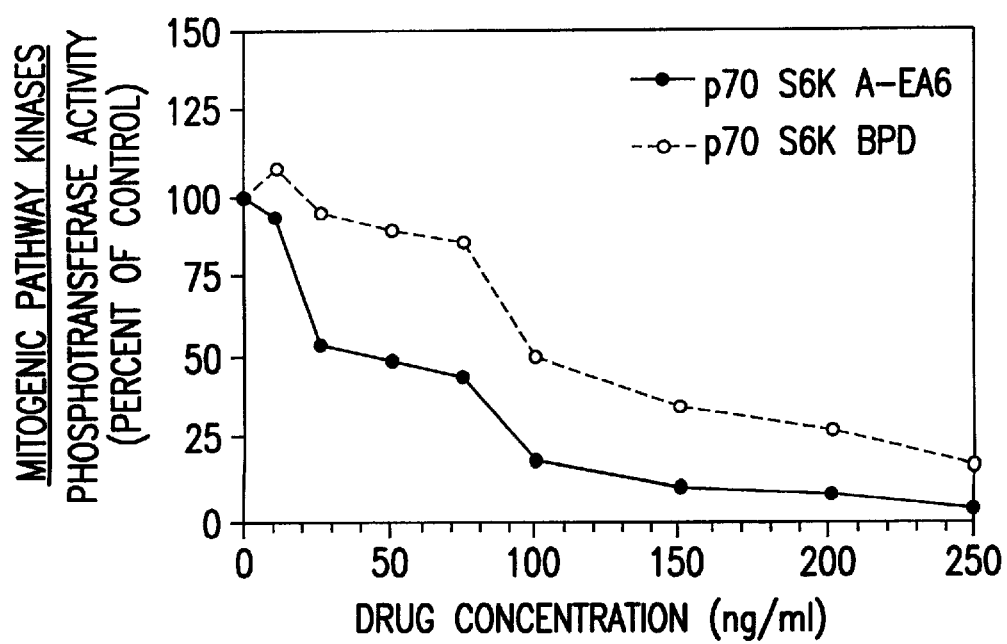
Figure 11C:
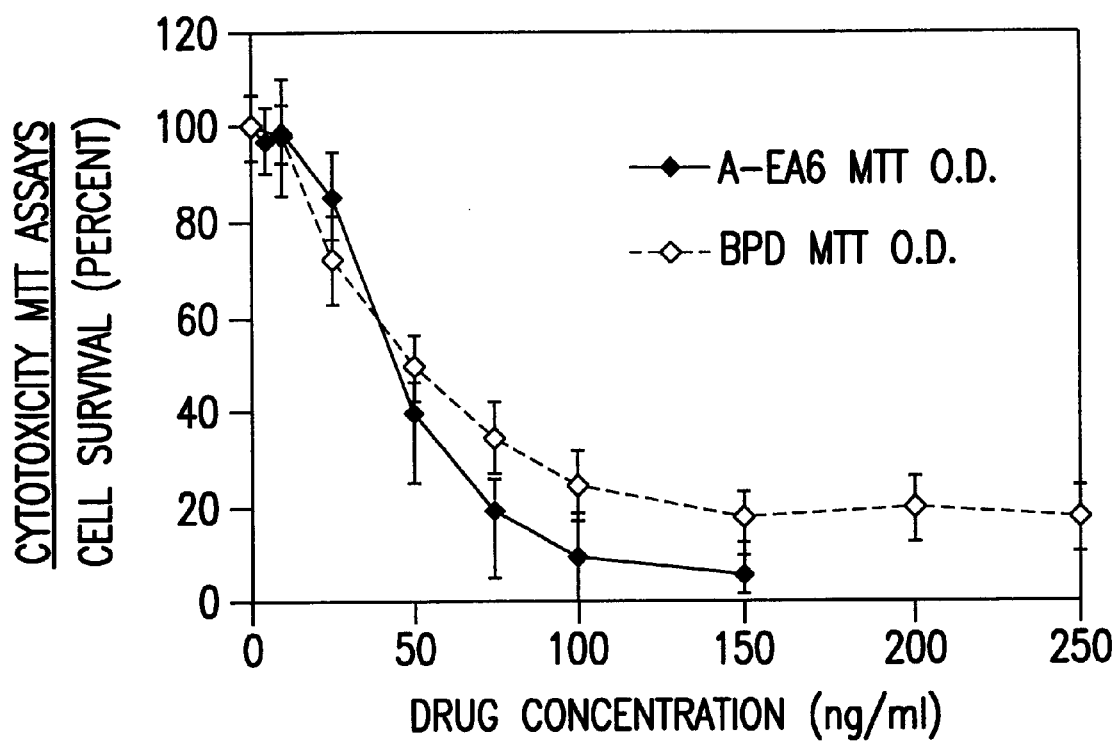

The conditions of the study set forth in Example 11 were repeated using HL-60 cells as the target and comparing the effects of A-EA6 and BPD-MA on cytotoxicity, on the mitogenic pathway kinase p70 S6K, and on the stress pathway kinases c-jun and HSP27. The results are shown in FIG. 11. At sublethal concentrations, A-EA6 showed stronger activation of the stress pathway kinases and stronger inhibition of the mitogenic pathway kinases.

Figure 12:
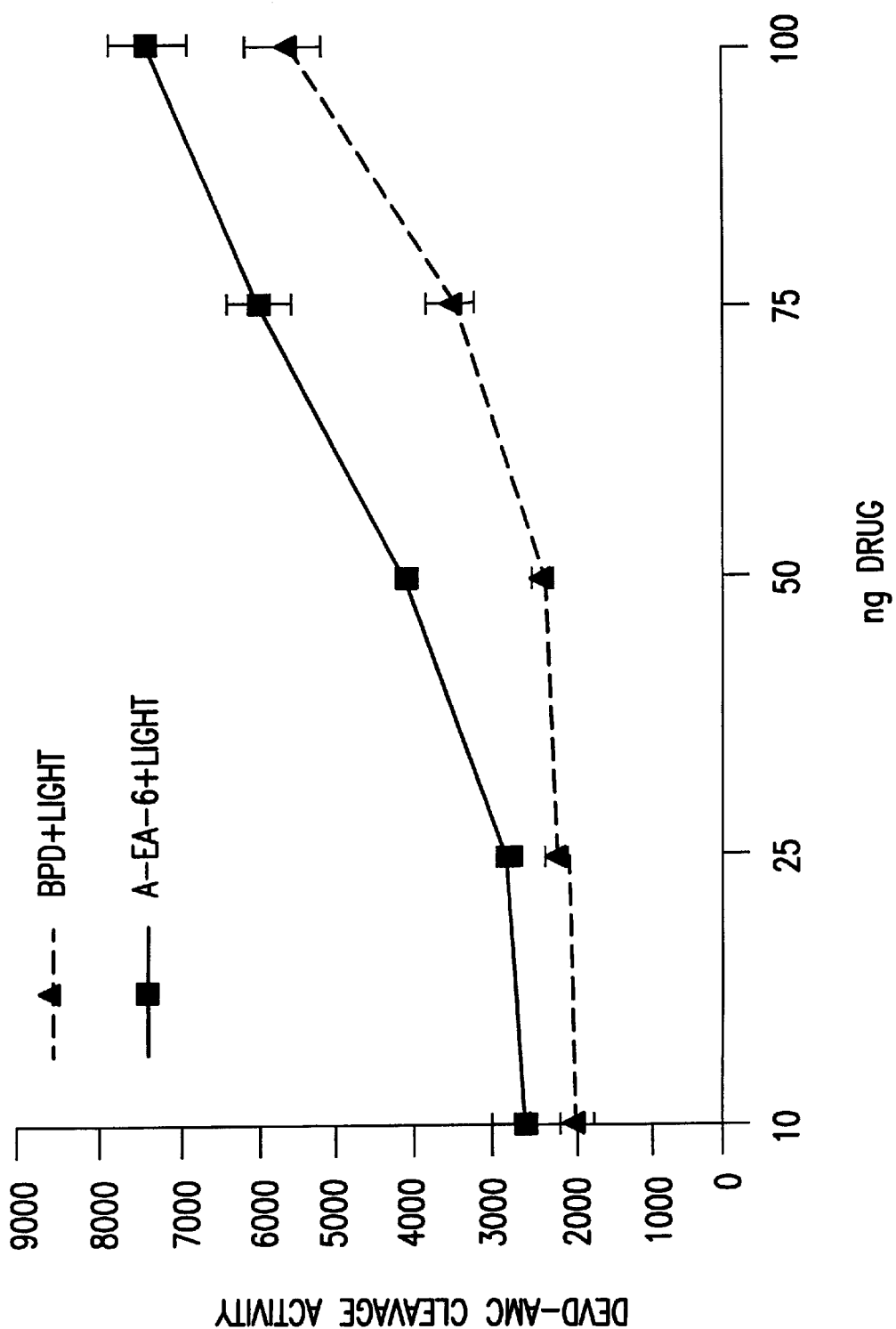
FIG. 12 shows the comparative effect of PDT using A-EA6 and BPD-MA on caspase activation in HL60 cells.

The effect on caspase activation in HL-60 cells was also measured. A-EA6 showed a stronger activation of caspases than did BPD-MA. This effect is desirable as it is associated with apoptosis. Using apoptosis to remove unwanted cells causes the least effect on surrounding normal cells and tissues. The comparison of A-EA6 with BPD-MA is shown in FIG. 12.

Figure 13:
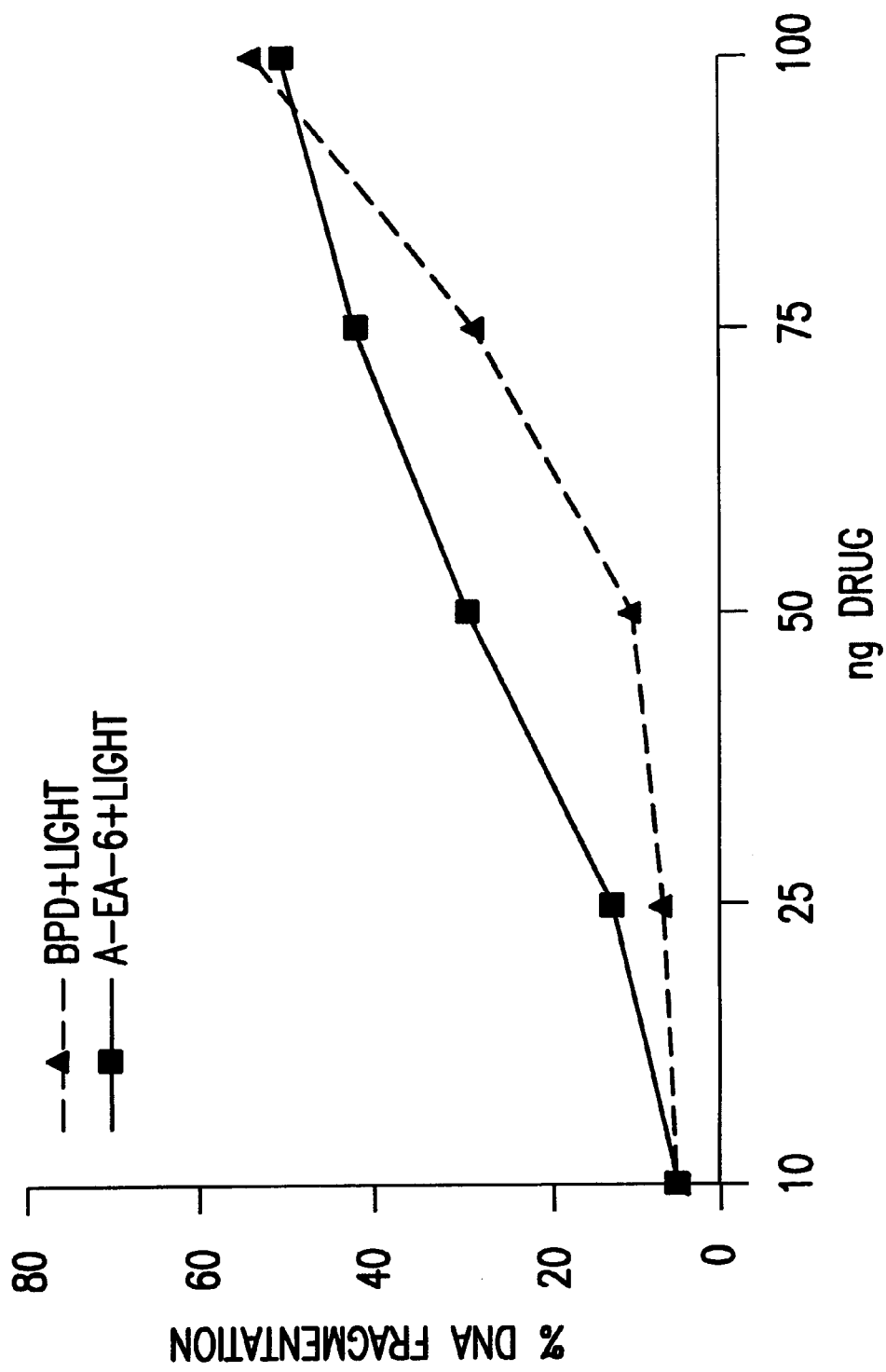
FIG. 13 shows the comparative effect of PDT using A-EA6 and BPD-MA on DNA fragmentation in HL60 cells.

FIG. 13 shows a similar comparison when percent DNA fragmentation was measured in HL-60 cells. Again, A-EA6 was effective at lower concentrations than BPD-MA.

EXAMPLE 13

In Vivo Photodynamic Therapy Using A-EA6

In a protocol similar to that set forth in Example 3, either A-EA6 or BPD-MA was injected intravenously into mice harboring M1 tumors at a dose of 1 mg/kg. This was followed by whole body irradiation with 50 J/cm² of 690 nm laser light at various times after administration of the drug. The number of tumor-free animals on day 7 was determined and the results are shown in Table 5.

TABLE 5

| Photosensitizer | Irradiation time (post i.v.) | Day 7 tumor-free animals |
|---|---|---|
| BPb-MA | 15 min | 10/10 |
|  | 30 min | 9/10 |
| A-EA6 | 15 min | 2/2 |
|  | 30 min | 6/6 |

These results show A-EA6 is at least as effective as BPD-MA in this assay.

EXAMPLE 14

Immunomodulatory Activity

Flanks of control and test mice were painted with the antigen DMFB and their ears were challenged 5 days later by pasting with the same compound. Test animals were treated with whole-body PDT using BPD-MA or A-EA6, by injecting the photosensitizer intravenously and then exposing the animals to red LED light at 15 J/cm$^2$. The percent suppression of ear swelling was calculated in comparison to controls. The results are shown in Table 6 and indicate that A-EA6 had a stronger immunomodulatory effect in this assay than did BPD-MA.

TABLE 6

| Photosensitizer | Dose (mg/kg) | Percent suppression |
|---|---|---|
| BPD-MA | 1.0 | 49% |
| A-EA8 | 1.0 | 68% |
| A-EA6 | 0.3 | 59% |

What is claimed:

1. A method for the treatment of tumors in a subject in need thereof comprising irradiating said subject with light after administration of a compound of the formula

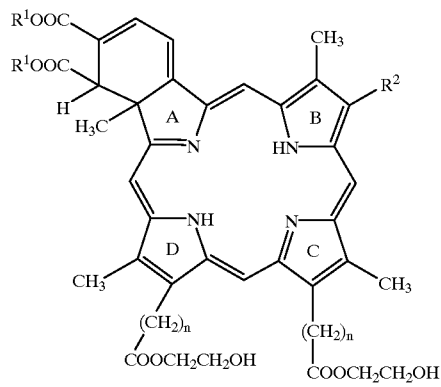

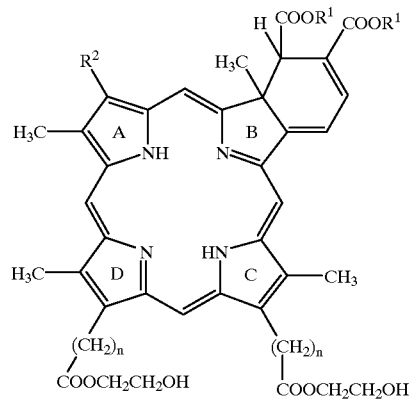

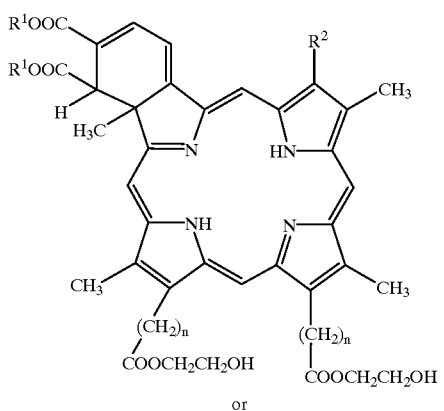

or

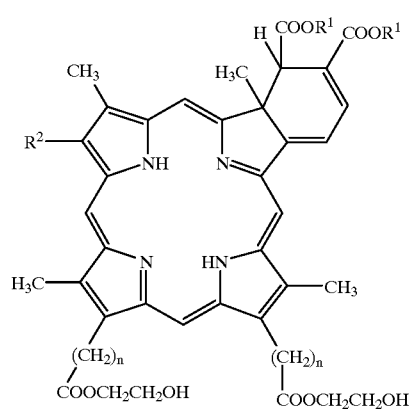

or their 1,4-diene isomers or the metallated and/or labeled and/or conjugated forms thereof wherein each R$^1$ is independently alkyl (1–6C);
each n is independently an integer of 0–6; and
R$^2$ is vinyl or a derivative thereof.

2. The method of claim 1 wherein in said compound, R$^2$ is vinyl, —CHOR', —CHO, —COOR', —CH(OR')CH$_3$, —CH(OR')CH$_2$ OR', —CH(SR')CH$_3$, —CH(NR')$_2$CH$_3$, —CH(CN)CH$_3$, —CH(COOR')CH$_3$, —CH(OOCR')CH$_3$, —CH(NR'COR')CH$_3$, —CH(CONR'$_2$)CH$_3$, —CH(halo)CH$_3$, or —CR(halo)CH$_2$(halo) wherein R' is H, or a hydrocarbon radical (1–6C) optionally substituted with a heteroatom substituent.

3. The method of claim 1 wherein in said compound, R$^2$ is an organic group of less than 12C resulting from derivatization of a vinyl substituent.

4. The method of claim 1 wherein in said compound, $R^2$ is a group containing 1–3 tetrapyrrole nuclei.

5. The method of claim 1 wherein said compound is in a metallated form.

6. The method of claim 1 wherein said compound is in conjugated form.

7. The method of claim 1 wherein said compound is labeled.

8. The method of claim 1 wherein said compound does not contain a metal ion.

9. The method of claim 1 wherein in said compound, $R^2$ is vinyl.

10. The method of claim 1 wherein in said compound, each $R^1$ is methyl.

11. The method of claim 1 wherein in said compound, both n are 2.

12. The method of claim 11 wherein in said compound, $R^2$ is vinyl and both $R^1$ are methyl.

13. The method of claim 1 wherein said compound is of formulas 1–4.

14. The method of claim 13 wherein in said compound, $R^2$ is vinyl, —CHOR', —CHO, —COOR', —CH(OR')CH$_3$, —CH(OR')CH$_2$OR', —CH(SR')CH$_3$, —CH(NR')$_2$CH$_3$, —CH(CN)CH$_3$, —CH(COOR')CH$_3$, —CH(OOCR')CH$_3$, —CH(NR'COR')CH$_3$, —CH(CONR'$_2$)CH$_3$, —CH(halo)CH$_3$, or —CH(halo)CH$_2$(halo) wherein R' is H, or a hydrocarbon radical (1–6C) optionally substituted with a heteroatom substituent.

15. The method of claim 13 wherein in said compound, $R^2$ is an organic group of less than 12C resulting from derivatization of a vinyl substituent.

16. The method of claim 13 wherein in said compound, $R^2$ is vinyl.

17. The method of claim 13 wherein in said compound, each $R^1$ is methyl.

18. The method of claim 13 wherein in said compound, both n are 2.

19. The method of claim 18 wherein in said compound, $R^2$ is vinyl and both $R^1$ are methyl.

20. The method of claim 12 wherein said compound is A-EA6 or B-EA6 or the metallated and/or labeled and/or conjugated forms thereof.

21. The method of claim 20 wherein said compound is in a metallated form.

22. The method of claim 20 wherein said compound is in conjugated form.

23. The method of claim 20 wherein said compound is labeled.

24. The method of claim 20 wherein said compound does not contain a metal ion.

* * * * *